US009848935B2

(12) United States Patent
Allen, IV et al.

(10) Patent No.: US 9,848,935 B2
(45) Date of Patent: Dec. 26, 2017

(54) SURGICAL INSTRUMENTS INCLUDING COMPONENTS AND FEATURES FACILITATING THE ASSEMBLY AND MANUFACTURING THEREOF

(71) Applicant: COVIDIEN LP, Mansfield, MA (US)

(72) Inventors: James D. Allen, IV, Broomfield, CO (US); Pawan Gujjala, Boudler, CO (US); Craig Krastins, Arvada, CO (US)

(73) Assignee: COVIDIEN LP, Mansfield, MA (US)

( * ) Notice: Subject to any disclaimer, the term of this patent is extended or adjusted under 35 U.S.C. 154(b) by 198 days.

(21) Appl. No.: 14/722,423

(22) Filed: May 27, 2015

(65) Prior Publication Data

US 2016/0345990 A1 Dec. 1, 2016

(51) Int. Cl.
*A61B 17/29* (2006.01)
*A61B 18/08* (2006.01)
(Continued)

(52) U.S. Cl.
CPC ........ *A61B 18/085* (2013.01); *A61B 17/2909* (2013.01); *A61B 18/1445* (2013.01);
(Continued)

(58) Field of Classification Search
CPC .............. A61B 17/00234; A61B 17/28; A61B 17/2812; A61B 17/2816; A61B 17/282; A61B 17/2841; A61B 17/29; A61B 17/2909; A61B 18/085; A61B 18/1442; A61B 18/1445; A61B 2017/0046;
(Continued)

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 9/2009
DE 2415263 A1 10/1975
(Continued)

OTHER PUBLICATIONS

Extended European Search Report issued in corresponding application No. 16171484.5 dated Sep. 5, 2016.
(Continued)

*Primary Examiner* — Ryan J Severson

(57) ABSTRACT

A surgical instrument includes a shell having a housing and a shaft. The shell including first and second shell components configured to engage one another to form the shell, each of which is monolithically formed to include a housing portion and a shaft portion. Upon engagement of the first and second shell components with one another, the housing portions cooperate to form the housing of the shell while the shaft portions cooperate to form the shaft of the shell. An end effector assembly is operably coupled to the shaft at a distal end of the shaft. A handle assembly is operably coupled to the housing. A drive assembly disposed within the shell is operably coupled between the handle assembly and the end effector assembly such that actuation of the handle assembly manipulates the end effector assembly.

14 Claims, 7 Drawing Sheets

(51) Int. Cl.
*A61B 18/14* (2006.01)
*A61B 17/00* (2006.01)

(52) U.S. Cl.
CPC ............... *A61B 2017/00526* (2013.01); *A61B 2017/2936* (2013.01)

(58) Field of Classification Search
CPC .. A61B 2017/00526; A61B 2017/2901; A61B 2017/291; A61B 2017/2912; A61B 2017/2913; A61B 2017/2916; A61B 2017/2918; A61B 2017/2925; A61B 2017/2926; A61B 2017/2932; A61B 2017/2933; A61B 2017/2936; A61B 2017/2937; A61B 2017/2938; A61B 2017/2939; A61B 2017/294; A61B 2017/2947

See application file for complete search history.

(56) References Cited

U.S. PATENT DOCUMENTS

| | | | |
|---|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| 5,326,013 A | 7/1994 | Green et al. |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,481,347 B2 * | 1/2009 | Roy .................... A61B 17/072 227/175.1 |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| 7,837,631 B2 | 11/2010 | Diamond et al. |
| D630,324 S | 1/2011 | Reschke |
| 7,935,052 B2 | 5/2011 | Dumbauld |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| 8,398,634 B2 | 3/2013 | Manzo et al. |
| D680,220 S | 4/2013 | Rachlin |
| 8,636,761 B2 | 1/2014 | Cunningham et al. |
| 2002/0062136 A1 | 5/2002 | Hillstead et al. |
| 2007/0173814 A1* | 7/2007 | Hixson .............. A61B 18/1445 606/51 |
| 2012/0101484 A1 | 4/2012 | Miersch |
| 2013/0066230 A1 | 3/2013 | Li et al. |
| 2013/0085516 A1 | 4/2013 | Kerr et al. |
| 2013/0345735 A1 | 12/2013 | Mueller |
| 2014/0025070 A1 | 1/2014 | Kerr et al. |
| 2014/0276723 A1 | 9/2014 | Parihar et al. |
| 2016/0345990 A1* | 12/2016 | Allen, IV .......... A61B 18/085 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |

(56) References Cited

FOREIGN PATENT DOCUMENTS

| JP | 11-169381 | A | 6/1999 |
|---|---|---|---|
| JP | 11-192238 | A | 7/1999 |
| JP | 11244298 | A | 9/1999 |
| JP | 2000-102545 | A | 4/2000 |
| JP | 2000-135222 | A | 5/2000 |
| JP | 2000342599 | A | 12/2000 |
| JP | 2000350732 | A | 12/2000 |
| JP | 2001008944 | A | 1/2001 |
| JP | 2001-29355 | | 2/2001 |
| JP | 2001029356 | A | 2/2001 |
| JP | 2001-03400 | | 4/2001 |
| JP | 2001128990 | A | 5/2001 |
| JP | 2001-190564 | A | 7/2001 |
| JP | 2002-136525 | A | 5/2002 |
| JP | 2002-528166 | A | 9/2002 |
| JP | 2003-116871 | A | 4/2003 |
| JP | 2003-175052 | A | 6/2003 |
| JP | 2003245285 | A | 9/2003 |
| JP | 2004-517668 | A | 6/2004 |
| JP | 2004-528869 | A | 9/2004 |
| JP | 2005-152663 | A | 6/2005 |
| JP | 2005-253789 | A | 9/2005 |
| JP | 2005312807 | A | 11/2005 |
| JP | 2006-015078 | A | 1/2006 |
| JP | 2006-501939 | A | 1/2006 |
| JP | 2006-095316 | A | 4/2006 |
| JP | 2008-054926 | A | 3/2008 |
| JP | 2011125195 | A | 6/2011 |
| SU | 401367 | A1 | 11/1974 |
| WO | 0036986 | A1 | 6/2000 |
| WO | 0059392 | A1 | 10/2000 |
| WO | 0115614 | A1 | 3/2001 |
| WO | 0154604 | A1 | 8/2001 |
| WO | 02/45589 | | 6/2002 |
| WO | 2004/032760 | A2 | 4/2004 |
| WO | 2006/021269 | A1 | 3/2006 |
| WO | 2005110264 | A3 | 4/2006 |
| WO | 2008/040483 | A1 | 4/2008 |
| WO | 2011/018154 | A1 | 2/2011 |

OTHER PUBLICATIONS

U.S. Appl. No. 14/098,953, filed Dec. 6, 2013; inventor: Cunningham.
U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Heniford et al. "Initial Research and Clinical Results with an Electrothermal Bipolar Vessel Sealer" Oct. 1999. (1 page).
Michael Choti, "Abdominoperineal Resection with the LigaSure Vessel Sealing System and LigaSure Atlas 20 cm Open Instrument"; Innovations That Work, Jun. 2003. (4 pages).
Chung et al., "Clinical Experience of Sutureless Closed Hemorrhoidectomy with LigaSure" Diseases of the Colon & Rectum vol. 46, No. 1 Jan. 2003, pp. 87-92.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).
Peterson et al. "Comparison of Healing Process Following Ligation with Sutures and Bipolar Vessel Sealing" Surgical Technology International (2001). (8 pages).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000. (1 page).
Johnson et al. "Evaluation of the LigaSure Vessel Sealing System in Hemorrhoidectormy" American College of Surgeons (ACS) Clinicla Congress Poster (2000). (1 page).
Muller et al., "Extended Left Hemicolectomy Using the LigaSure Vessel Sealing System" Innovations That Work, Sep. 1999. (4 pages).
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002. (4 pages).
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002. (4 pages).
Koyle et al., "Laparoscopic Palomo Varicocele Ligation in Children and Adolescents" Pediatric Endosurgery & Innovative Techniques, vol. 6, No. 1, 2002, pp. 15-19.
W. Scott Helton, "LigaSure Vessel Sealing System: Revolutionary Hemostasis Product for General Surgery"; Sales/Product Literature 1999. (1 page).
LigaSure Vessel Sealing System, the Seal of Confidence in General, Gynecologic, Urologic, and Laparaoscopic Surgery; Sales/Product Literature; Apr. 2002. (8 pages).
Joseph Ortenberg "LigaSure System Used in Laparoscopic 1st and 2nd Stage Orchiopexy" Innovations That Work, Nov. 2002. (4 pages).
Sigel et al. "The Mechanism of Blood Vessel Closure by High Frequency Electrocoagulation" Surgery Gynecology & Obstetrics, Oct. 1965 pp. 823-831.

(56) References Cited

OTHER PUBLICATIONS

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001. (8 pages).

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.

"Reducing Needlestick Injuries in the Operating Room" Sales/Product Literature 2001. (1 page).

Bergdahl et al. "Studies on Coagulation and the Development of an Automatic Computerized Bipolar Coagulator" J. Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003. (15 pages).

Dulemba et al. "Use of a Bipolar Electrothermal Vessel Sealer in Laparoscopically Assisted Vaginal Hysterectomy" Sales/Product Literature; Jan. 2004. (1 page).

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000. (1 page).

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000. (4 pages).

Levy et al. "Use of a New Energy-based Vessel Ligation Device During Vaginal Hysterectomy" Int'l Federation of Gynecology and Obstetrics (FIGO) World Congress 1999. (1 page).

Barbara Levy, "Use of a New Vessel Ligation Device During Vaginal Hysterectomy" FIGO 2000, Washington, D.C.. (1 page).

E. David Crawford "Use of a Novel Vessel Sealing Technology in Management of the Dorsal Veinous Complex" Sales/Product Literature 2000. (1 page).

Jarrett et al., "Use of the LigaSure Vessel Sealing System for Peri-Hilar Vessels in Laparoscopic Nephrectomy" Sales/Product Literature 2000. (1 page).

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.. (1 page).

McLellan et al. "Vessel Sealing for Hemostasis During Gynecologic Surgery" Sales/Product Literature 1999. (1 page).

U.S. Appl. No. 08/926,869, filed Sep. 10, 1997; inventor: James G. Chandler.

U.S. Appl. No. 09/177,950, filed Oct. 23, 1998; inventor: Randel A. Frazier.

U.S. Appl. No. 09/387,883, filed Sep. 1, 1999; inventor: Dale F. Schmaltz.

U.S. Appl. No. 09/591,328, filed Jun. 9, 2000; inventor: Thomas P. Ryan.

U.S. Appl. No. 12/336,970, filed Dec. 17, 2008; inventor: Paul R. Sremeich.

U.S. Appl. No. 14/065,644, filed Oct. 29, 2013; inventor: Reschke.

* cited by examiner

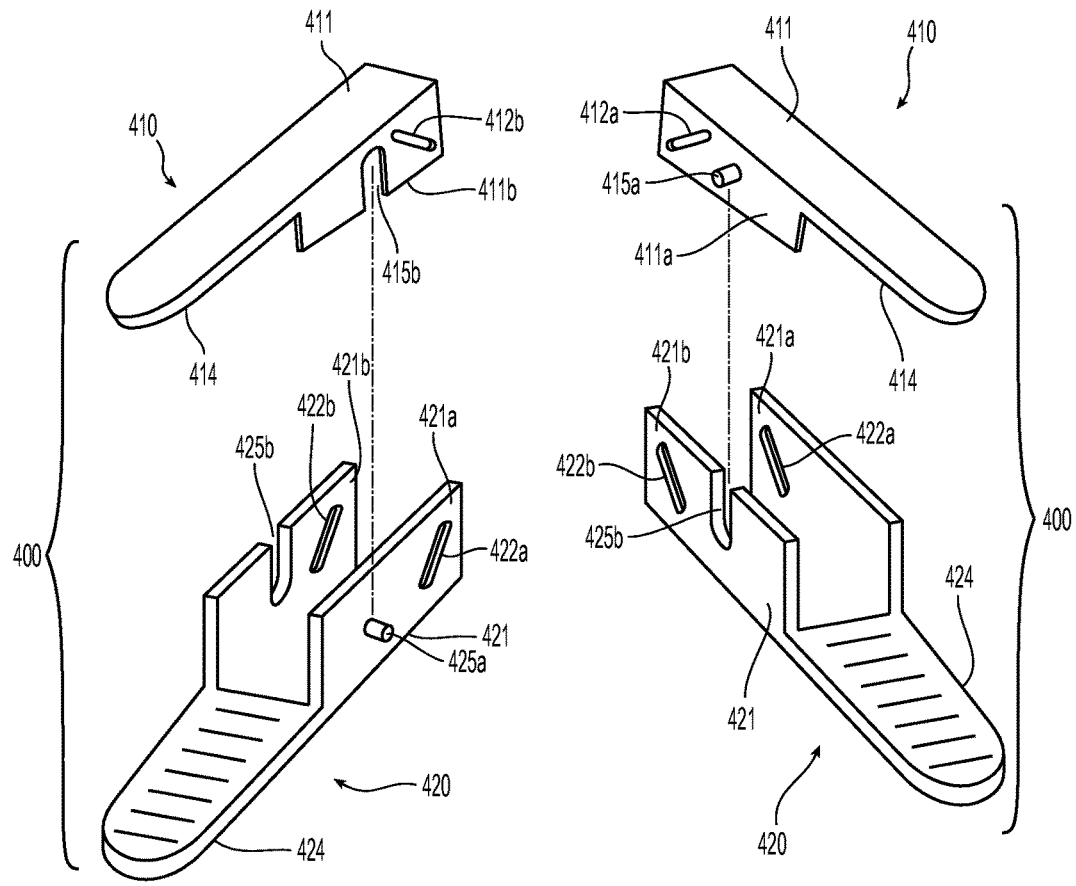
*Fig. 6A*        *Fig. 6B*
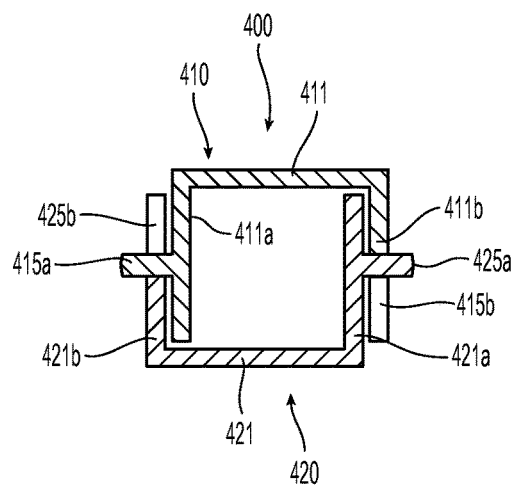
*Fig. 7*

SURGICAL INSTRUMENTS INCLUDING COMPONENTS AND FEATURES FACILITATING THE ASSEMBLY AND MANUFACTURING THEREOF

BACKGROUND

Technical Field

The present disclosure relates to surgical instruments and, more particularly, to surgical forceps configured for treating tissue and including components and/or features that facilitate the assembly and manufacture thereof.

Background of Related Art

A surgical forceps is a plier-like device which relies on mechanical action between its jaws to grasp, clamp, and constrict tissue. Energy-based surgical forceps utilize both mechanical clamping action and energy to treat, e.g., coagulate, cauterize, and/or seal, tissue.

Generally, surgical instruments, including surgical forceps, can be classified as disposable instruments, e.g., instruments that are discarded after a single use, or reusable instruments, e.g., instruments capable of being sterilized for repeated use. As can be appreciated, those instruments that are configured for single-use must be cost-efficient while still being capable of effectively performing their intended functions.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A surgical instrument provided in accordance with aspects of the present disclosure includes a shell having a housing and a shaft extending distally from the housing. The shell includes first and second shell components configured to engage one another to form the shell. Each of the first and second shell components is monolithically formed and includes a housing portion and a shaft portion. The housing portions cooperate to form the housing of the shell upon engagement of the first and second shell components with one another. The shaft portions cooperate to form the shaft of the shell upon engagement of the first and second shell components with one another. An end effector assembly is operably coupled to the shaft at a distal end of the shaft. A handle assembly is operably coupled to the housing. A drive assembly is disposed within the shell and operably coupled between the handle assembly and the end effector assembly such that actuation of the handle assembly manipulates the end effector assembly.

In an aspect of the present disclosure, each of the first and second shell components is a single molded piece.

In another aspect of the present disclosure, the housing portions each include a fixed handle portion extending therefrom. The fixed handle portions cooperate to define a fixed handle of the handle assembly upon engagement of the first and second shell components with one another. The fixed handle portions may be monolithically formed with the respective housing portions thereof. Further, the handle assembly may include a movable handle pivotably coupled between the housing portions and movable relative to the fixed handle.

In yet another aspect of the present disclosure, the first and second shell components each include engagement features monolithically formed therewith to facilitate the engagement of the first and second shell components with one another.

In still another aspect of the present disclosure, the first and second shell components each include support structures monolithically formed therewith to facilitate the support of the drive assembly within the shell.

In still yet another aspect of the present disclosure, the end effector assembly includes first and second jaw members. One or both of the first and second jaw members is pivotable relative to the other between a spaced-apart position and an approximated position for grasping tissue therebetween.

In another aspect of the present disclosure, one of the jaw members is fixed relative to the shaft and the other jaw member is movable relative to the fixed jaw member and the shaft between the spaced-apart and approximated positions. In such aspects, the fixed jaw member may include a proximal flange that is monolithically formed with the shaft portion of one of the first and second shell components, or may include first and second flange components monolithically formed with the respective shaft portions of the first and second shell components and configured to engage one another to form the proximal flange upon engagement of the first and second shell components with one another.

In yet another aspect of the present disclosure, one or both of the first and second jaw members is configured to engage the shaft via a peg-aperture engagement.

In still another aspect of the present disclosure, one or both of the first and second jaw members is configured to engage the drive assembly via a pin-slot engagement or a peg-slot engagement.

In still yet another aspect of the present disclosure, each of the first and second jaw members includes a "U"-shaped proximal flange portion. In such aspects, the "U"-shaped proximal flange portions are configured to inter-fit with one another in an overlapping configuration.

In another aspect of the present disclosure, the shaft includes a pair of spaced-apart flanges extending from the distal end of the shaft and coupled to the shaft via living hinges. The spaced-apart flanges are configured to flex relative to the shaft to facilitate engagement of the end effector assembly with the shaft.

BRIEF DESCRIPTION OF THE DRAWINGS

Various aspects and features of the present disclosure described herein with reference to the drawings wherein:

FIG. 6A is an exploded, left side perspective view of another end effector assembly provided in accordance with the present disclosure;

FIG. 6B is an exploded, right side perspective view of the end effector assembly of FIG. 6A;

FIG. 7 is a transverse, cross-sectional view of the proximal flange portions of the jaw members of the end effector assembly of FIG. 6A.

DETAILED DESCRIPTION

Figure 1:
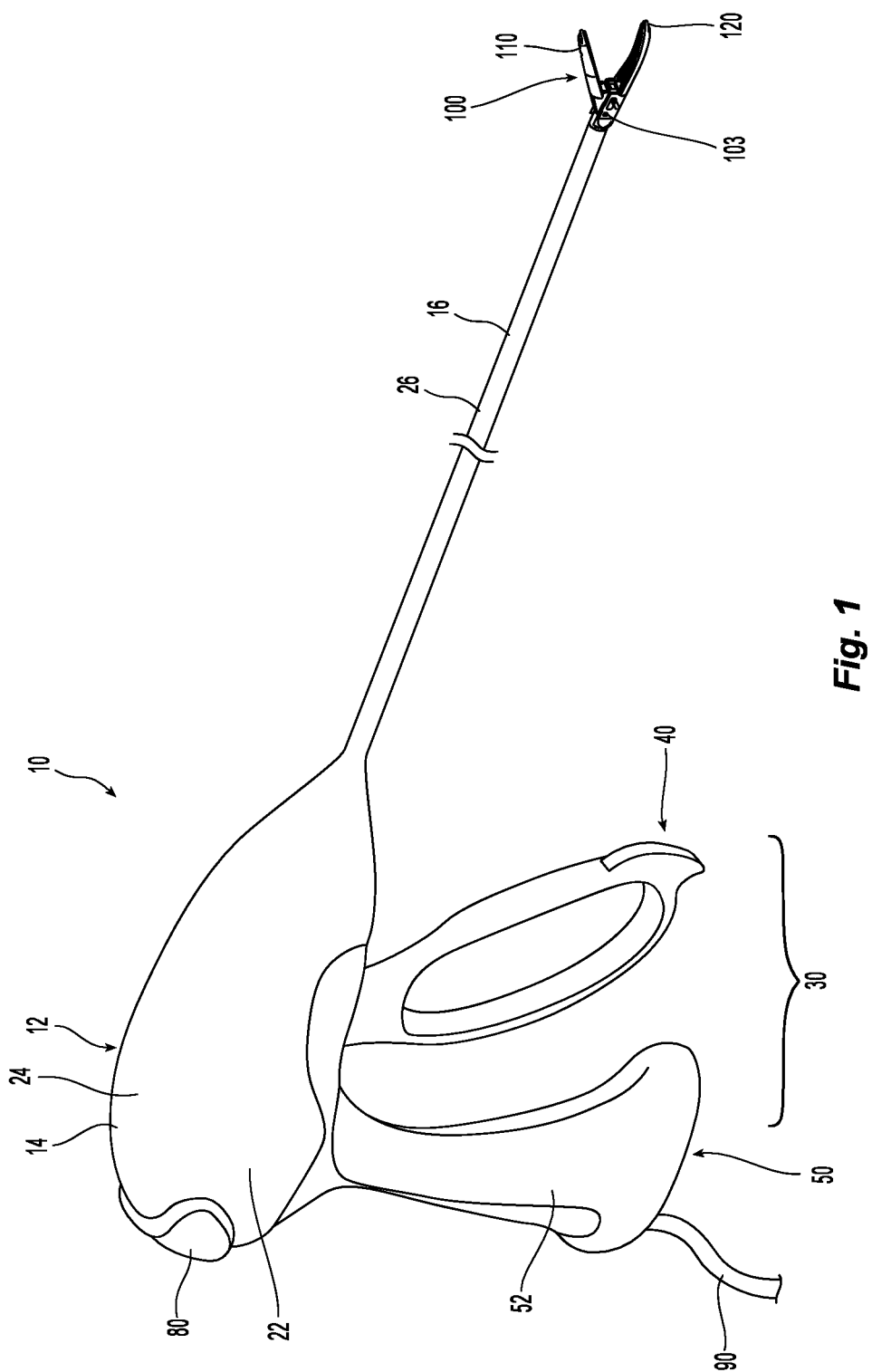
FIG. 1 is a perspective view of a surgical forceps provided in accordance with the present disclosure.

Referring to FIG. 1, an embodiment of a surgical forceps provided in accordance with the present disclosure is shown generally identified by reference numeral 10. Although surgical forceps 10 is shown configured for use in connection with endoscopic surgical procedures, the present disclosure is equally applicable for use in more traditional open surgical procedures and with any suitable surgical instrument.

Forceps 10 generally includes a shell 12 defining a proximal housing portion 14 and a distal shaft portion 16 extending distally from proximal housing portion 14. Forceps 10 further includes a handle assembly 30, an activation switch 80, and an end effector assembly 100. A cable 90 connects forceps 10 to an energy source (not shown), e.g., a generator or other suitable power source, although forceps 10 may alternatively be configured as a battery-powered device. Cable 90 includes a wire (or wires) (not shown) extending therethrough that has sufficient length to extend through proximal housing portion 14 and distal shaft portion 16 of shell 12 in order to provide energy to one or both of respective tissue-treating surfaces 114, 124 (FIG. 3) of jaw members 110, 120 of end effector assembly 100. However, energy may alternatively be supplied to respective tissue-treating surfaces 114, 124 (FIG. 3) of jaw members 110, 120 in any other suitable fashion, e.g., via conductive structural components of forceps 10, brush-contacts, etc. Activation switch 80 is coupled between tissue-treating surfaces 114, 124 (FIG. 3) of jaw members 110, 120, respectively, and the source of energy (not shown) for enabling the selective supply of energy to tissue-treating surfaces 114, 124 (FIG. 3) of jaw members 110, 120 for treating tissue grasped therebetween.

Figure 2A:
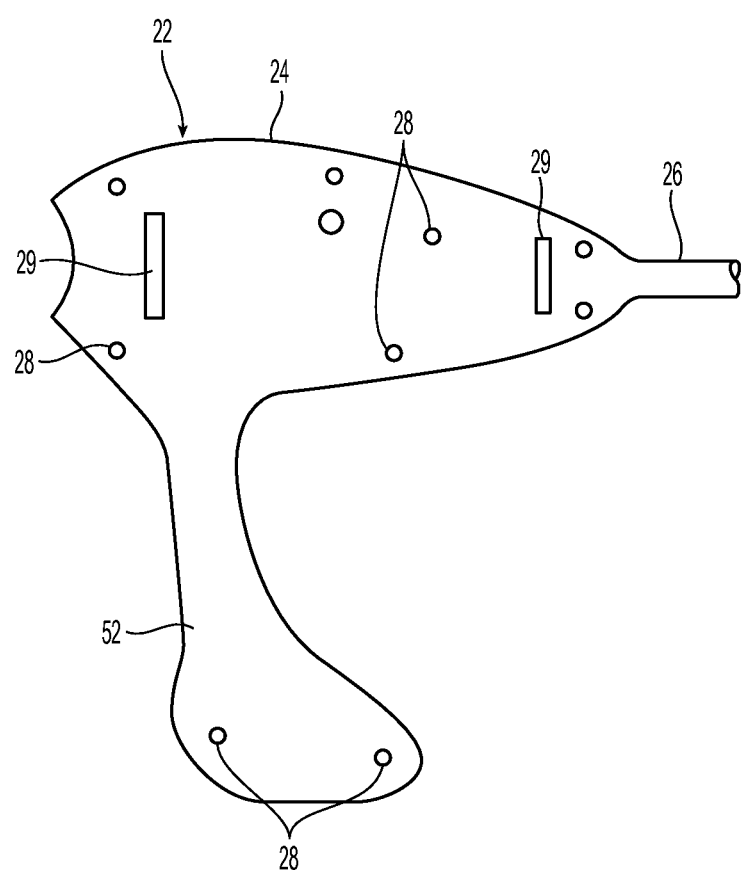
FIG. 2A is a side view of one of the shell components forming the shell of the forceps of FIG. 1A.

With additional reference to FIG. 2A, shell 12 is formed from two shell components 22 that are secured to one another to fully form shell 12. Each shell component 22 forms one-half of shell 12, although other configurations are also contemplated, and includes a proximal housing component portion 24 and a distal shaft component portion 26 extending distally from the respective proximal housing component portion 24. Each shell component 22 is monolithically formed as a single-piece, e.g., via injection molding or other suitable manufacturing process. As can be appreciated, proximal housing component portions 24 of shell components 22 cooperate to form proximal housing portion 14 of shell 12 upon assembly of shell components 22, and distal shaft component portions 26 of shell components 22 cooperate to form distal shaft portion 16 of shell 12 upon assembly of shell components 22. Shell components 22 may include suitable features, e.g., complementary peg/aperture engagement features 28, to enable press-fitting or snap-fitting of shell components 22 with one another, although other suitable engagements are also contemplated. Shell components 22 each further include support structures 29 configured to support the internal operating components of shell 12, e.g., movable handle 40 and drive assembly 60 (FIG. 2B), as detailed below.

The above-detailed configuration of shell 12 is advantageous at least in that the need to secure a shaft with a housing is obviated. Rather, since shell components 22 are monolithically-formed to each include both a proximal housing component portion 24 and a distal shaft component portion 26, the integrated housing-shaft defined by shell 12 is formed upon engagement of shell components 22 with one another.

Figure 2B:
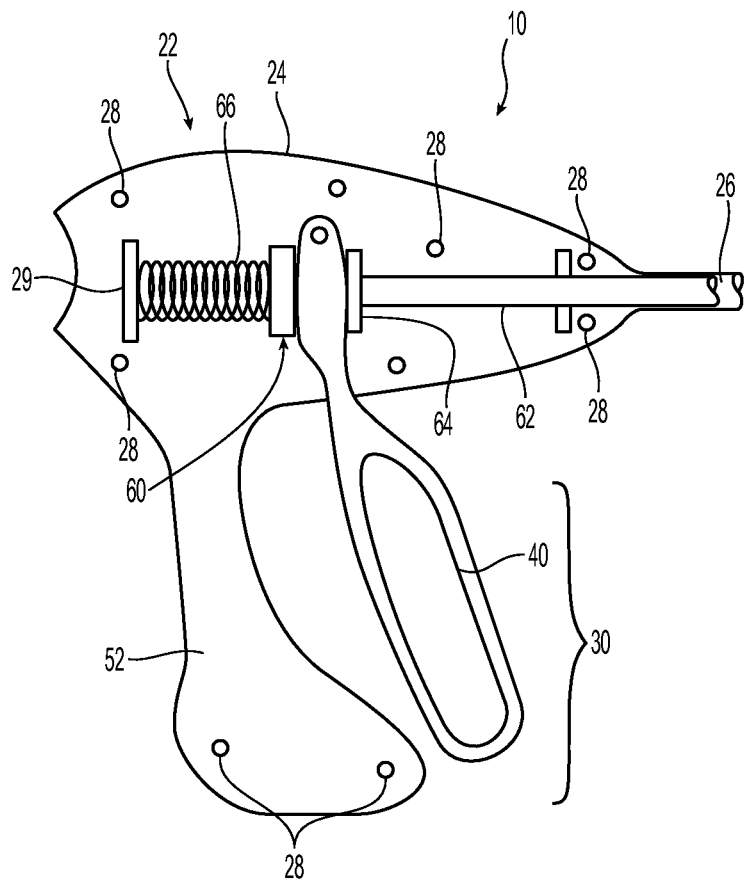
FIG. 2B is a side view of the shell component of FIG. 2A including the movable handle and drive assembly of the forceps of FIG. 1 operably coupled therewith.

Referring to FIGS. 1 and 2B, handle assembly 30 includes a fixed handle 50 and a movable handle 40. Fixed handle 50 is formed from handle component portions 52 of shell components 22 that are integrally associated with the proximal housing component portion 24 of the respective shell component 22 such that fixed handle 50 is fully formed upon engagement of shell components 22 with one another to form shell 12. Movable handle 40 of handle assembly 30 is operably coupled to shell 12 and a drive assembly 60 that, together, mechanically cooperate to impart movement of one or both of jaw members 110, 120 of end effector assembly 100 about a pivot 103 and relative to distal shaft portion 16 of shell 12 between a spaced-apart position and an approximated position to grasp tissue between jaw members 110, 120. In the illustrated embodiment, movable handle 40 is coupled to drive bar 62 via a drive mandrel 64 such that movement of movable handle 40 relative to fixed handle 50 effects longitudinal translation of drive bar 62 through proximal housing portion 14 and distal shaft portion 16 of shell 12. Movable handle 40 is pivotably coupled to shell 12 within proximal housing portion 14 thereof, while support structures 29 support drive assembly 60 within proximal housing portion 14 of shell 12.

Figure 3:
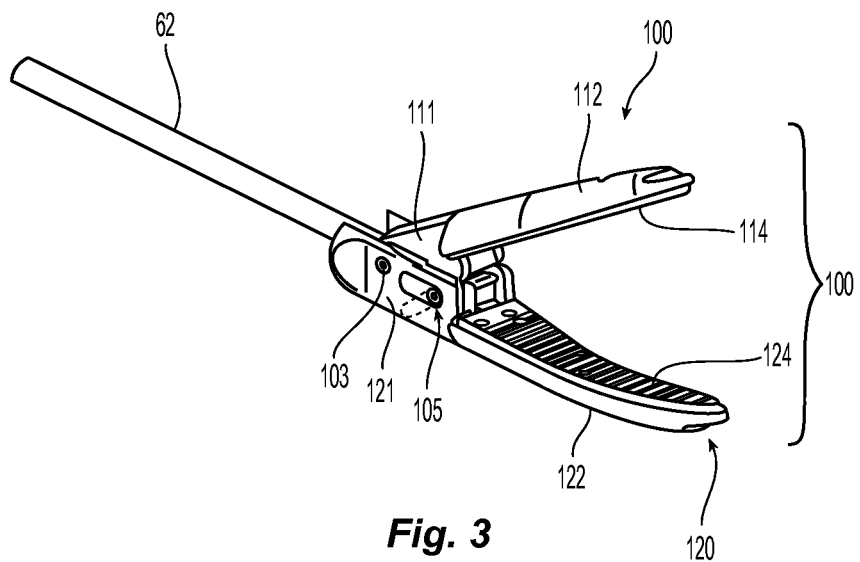
FIG. 3 is an enlarged, perspective view of the end effector assembly of the forceps of FIG. 1, including a drive bar of the drive assembly operably coupled therewith.

With additional reference to FIG. 3, the distal end of drive bar 62 is coupled to one or both jaw members 110, 120, e.g., via a cam-slot coupling 105, such that longitudinal translation of drive bar 62 relative to end effector assembly 100 pivots one or both of jaw members 110, 120 relative to one another. As shown in FIG. 1, movable handle 40 is initially spaced-apart from fixed handle 50 and, correspondingly, jaw members 110, 120 are disposed in the spaced-apart position. Movable handle 40 is depressible from this initial position to a depressed position corresponding to the approximated position of jaw members 110, 120. A biasing member 66 may be disposed about drive bar 62 and positioned to bias drive bar 62 distally, thereby biasing jaw members 110, 120 towards the spaced-apart position and movable handle 40 apart from fixed handle 50. However, other configurations for biasing jaw members 110, 120 towards the spaced-apart position and/or positions of biasing member 66 for accomplishing the same are also contemplated.

Continuing with reference to FIG. 3, each jaw member 110, 120 of end effector assembly 100 includes a proximal flange 111, 121 and a distal jaw body including an outer insulative jaw housing 112, 122 and a tissue-treating surface 114, 124, respectively. Alternatively, one of both of jaw members 110, 12 may be monolithically formed from a conductive material. Proximal flanges 111, 121 are pivotably coupled to one another and distal shaft portion 16 of shell 12 about pivot 103 and operably coupled to drive bar 62 via cam-slot coupling 105 for enabling movement of jaw members 110, 120 between the spaced-apart and approximated positions upon depression of movable handle 40, as noted above.

End effector assembly 100 may be configured as a unilateral assembly (as shown), i.e., wherein one of the jaw members, e.g., jaw member 120, is fixed relative to distal shaft portion 16 of shell 12 and the other jaw member, e.g., jaw member 110, is movable about pivot 103 relative to distal shaft portion 16 of shell 12 and the fixed jaw member 120. Alternatively, end effector assembly 100 may be designed as a bilateral assembly, i.e., wherein both jaw member 110 and jaw member 120 are movable about pivot 103 relative to one another and to distal shaft portion 16 of shell 12. Where a unilateral configuration is utilized, proximal flange 121 of jaw member 120 may be secured to distal shaft portion 16 of shell 12 after assembly of shell 12. Alternatively, the proximal flange 121 of jaw member 120 may be monolithically formed with one of the distal shaft component portions 26 of shell 12, or may be formed via cooperating components that are monolithically formed with respective distal shaft component portions 26 such that jaw member 120 is fully formed upon assembly of shell 12, e.g., via engagement of the cooperating components. Further, pivot 103 may be monolithically formed with either or both of shell components 22 such that, upon assembly of shell 12, pivot pin 103 operably engages jaw member 110 and/or jaw member 120 therewith. Other configurations to facilitate operable engagement of end effector assembly 100 with shell 12 are detailed below with respect to FIGS. 4-7.

Detailed below with respect to FIGS. 4-7 are embodiments of various configurations of end effector assemblies, distal shaft portions, and/or drive assemblies that facilitate operable engagement therebetween, thus facilitating assembly. These end effector assemblies, shaft portions, and/or drive assemblies may be similar to and may include any of the features of those detailed above with respect to forceps 10 (FIG. 1). Alternatively, the aspects and features detailed below may be utilized in conjunction with any other suitable surgical instrument. For purposes of brevity, only the differences between the configurations detailed with respect to FIGS. 4-7 and those of forceps 10 (FIG. 1) are detailed below, while similarities will be summarily described or omitted entirely.

Figure 4:
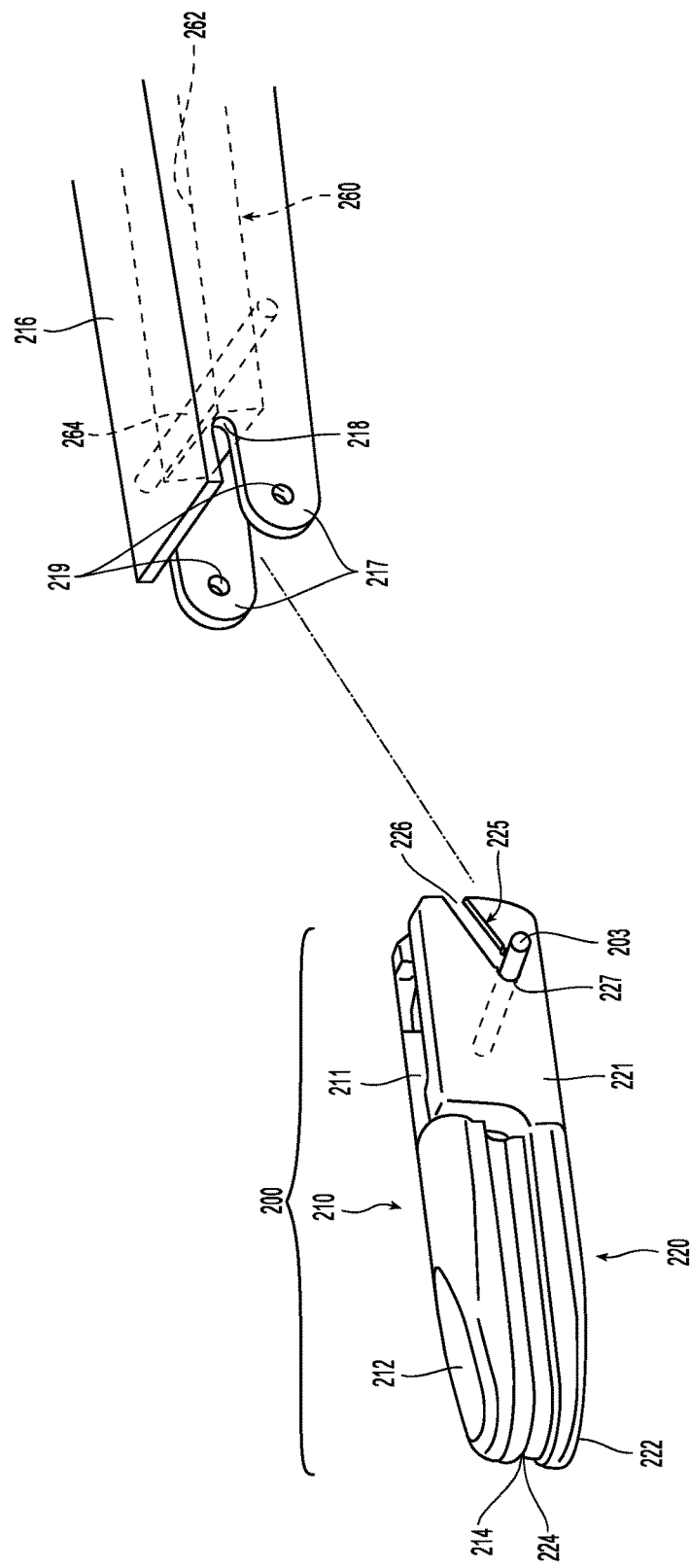
FIG. 4 is an exploded view of the distal end components of another forceps provided in accordance with the present disclosure.

Referring to FIG. 4, end effector assembly 200 is similar to end effector assembly 100 (FIG. 3) and generally includes first and second jaw members 210, 220 each including a proximal flange 211, 221 and a distal jaw body including an outer jaw housing 212, 222 and a tissue-treating surface 214, 224, respectively, similarly as detailed above with respect to end effector assembly 100 (FIG. 3). Proximal flanges 211, 221 each define a cam slot 225 (only the cam slot of proximal flange 221 of jaw members 220 is shown). Cam slots 225 are oppositely angled relative to one another and define open proximal ends 226 and closed distal end 227. Proximal flanges 211, 221 are pivotably coupled to one another about a pivot pin 203 that is captured within closed distal ends 227 of cam slots 225. Pivot pin 203 extends outwardly from either side of end effector assembly 200. The above-detailed configuration of end effector assembly 200 allows end effector assembly 200 to be assembled as a sub-unit, ultimately to be coupled with the remainder of the forceps, as detailed below.

Continuing with reference to FIG. 4, distal shaft portion 216 defines a generally rectangular configuration, although other configurations are also contemplated, and includes drive bar 262 of drive assembly 260 slidably disposed therein. Distal shaft portion 216 and drive assembly 260 may cooperate with a proximal housing portion and handle assembly similarly as detailed above with respect to forceps 10 (FIGS. 1-3) or with any other suitable components. Distal shaft portion 216 includes, at its distal end thereof, a pair of opposed flanges 217 that are resiliently coupled with the body of distal shaft portion 216 via living hinges 218. As such, at least some degree of outward flexion of flanges 217 relative to distal shaft portion 216 is permitted. Each flange 217 further defines a transverse aperture 219 therethrough. Apertures 219 of flanges 217 are aligned with one another. Drive bar 262 includes a transverse drive pin 264 coupled thereto towards or at the distal end thereof.

In order to operably engage the sub-unit end effector assembly 200 with the forceps, e.g., with distal shaft portion 216 and drive assembly 260, one or both of flanges 217 is flexed outwardly to permit end effector assembly 200 to be at least partially inserted therebetween and positioned such that the ends of pivot pin 203, which extend outwardly from either side of end effector assembly 200, are engaged within transverse apertures 219 of flanges 217. Thereafter, the flange 217 or flanges 217 may be released, allowing flange(s) 217 to resiliently return to the at-rest position, capturing pivot pin 203 therebetween and pivotably engaging end effector assembly 200 between flanges 217.

As end effector assembly 200 is moved into position between flanges 217, as detailed above, transverse drive pin 264 of drive bar 262 is inserted into open proximal ends 226 of cam slots 225, in operable engagement therewith. Thus, in use, upon translation of drive bar 262 relative to distal shaft portion 216 and end effector assembly 200, transverse drive pin 264 is moved along the oppositely-angled cam slots 225 of jaw members 210, 220 to thereby pivot jaw members 210, 220 relative to one another, e.g., between spaced-apart and approximated positions.

Figure 5:
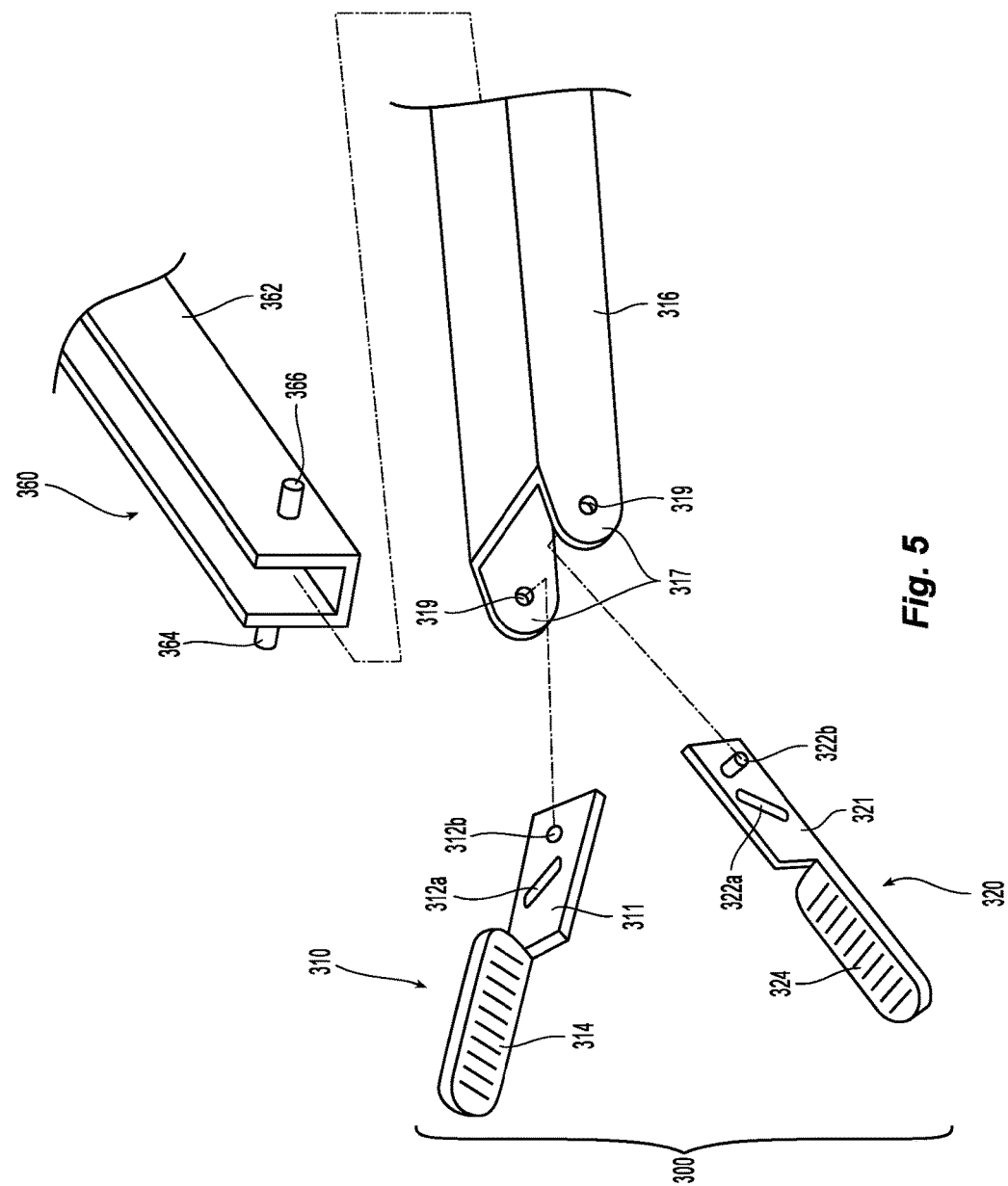
FIG. 5 is an exploded view of the distal end components of yet another forceps provided in accordance with the present disclosure.

Referring to FIG. 5, end effector assembly 300 is similar to end effector assemblies 100, 200 (FIGS. 3 and 4, respectively) and generally includes first and second jaw members 310, 320 each including a proximal flange 311, 321 and a distal jaw body defining a tissue-treating surface 314, 324, respectively. Proximal flanges 311, 321 each define an oppositely-angled cam slot 312a, 322a. Proximal flanges 311, 321 each further include pivot pegs 312b, 322b extending outwardly therefrom.

Continuing with reference to FIG. 5, distal shaft portion 316 defines a generally rectangular configuration, although other configurations are also contemplated, and includes drive bar 362 of drive assembly 360 slidably disposed therein. Distal shaft portion 316 and drive assembly 360 may cooperate with a proximal housing portion and handle assembly similarly as detailed above with respect to forceps 10 (FIGS. 1-3) or with any other suitable components. Distal shaft portion 316 includes, at its distal end thereof, a pair of flanges 317, each of which defines a transverse aperture 319 therethrough. Drive bar 362 includes first and second drive pin pegs 364, 366 disposed towards the distal end thereof and extend outwardly from respective first and second sides of drive bar 362. Flanges 317 of distal shaft portion 316 and/or drive bar 362 may define some degree of flexibility to facilitate assembly, as detailed below, although rigid configurations are also contemplated.

In order to operably engage jaw members 310, 320 of end effector assembly 300 with the forceps, e.g., with distal shaft portion 316 and drive assembly 360, one of the jaw members, e.g., jaw member 310, is first manipulated into position such that pivot peg 312b is received within aperture 319 of one of flanges 317 and such that drive pin peg 364 of drive bar 362 is received within cam slot 312a. Thereafter, the other jaw members, e.g., jaw member 320, is manipulated into position such that pivot peg 322b is received within aperture 319 of the other flange 317 and such that drive pin peg 366 of drive bar 362 is received within cam slot 322a. Interference between the various components, e.g., proximal flanges 311, 321, drive bar 362, and distal shaft portion 316, inhibits disengagement of jaw members 310, 320 from distal shaft portion 316 and drive assembly 360 once fully assembled. Similarly as detailed above, in use, upon translation of drive bar 362 relative to distal shaft portion 316 and end effector assembly 300, drive pin pegs 364, 366 are moved along the oppositely-angled cam slots 312a, 322a of jaw members 310, 320 to thereby pivot jaw members 310, 320 relative to one another, e.g., between spaced-apart and approximated positions.

Referring to FIGS. 6A-7, end effector assembly 400 is similar to end effector assemblies 100, 200, 300 (FIGS. 3, 4, and 5, respectively) and generally includes first and second jaw members 410, 420 each including a proximal flange portion 411, 421 and a distal jaw body defining a tissue-treating surface 414, 424, respectively. Proximal flange portions 411, 421 each define a "U"-shaped configuration having a pair of spaced-apart uprights 411a, 411b and 421a, 421b. Each upright 411a, 411b and 421a, 421b defines a cam slot 412a, 412b and 422a, 422b, respectively, with the cam slots 412a, 412b of proximal flange portion 411 being angled oppositely relative to the cam slots 422a, 422b of proximal flange portion 421. One of the uprights 411a, 421a of each proximal flange portion 411, 421 includes a pivot peg 415a, 425a extending outwardly therefrom while the other upright 411b, 421b of each proximal flange portion 411, 421 includes an open vertical slot 415b, 425b defined therein.

During assembly of end effector assembly 400, proximal flange portions 411, 421 are configured to inter-fit with one another in overlapping relation, as illustrated, for example, in FIG. 7. More specifically, proximal flange portions 411, 421 are positioned such that pivot peg 415a of upright 411a of proximal flange portion 411 is received within open vertical slot 425b of upright 421b of proximal flange portion 421 and such that pivot peg 425a of upright 421a of proximal flange portion 421 is received within open vertical slot 415b of upright 411b of proximal flange portion 411, thereby pivotably coupling jaw members 410, 420 to one another.

In the assembled condition of jaw members 410, 420 of end effector assembly 400, pivot pegs 415a, 425b extend outwardly from either side of end effector assembly 400, thus facilitating the eventual pivotable engagement within transverse apertures defined within the distal shaft portion of a forceps, e.g., similarly as detailed above with respect to end effector assembly 200 (FIG. 4) or end effector assembly 300 (FIG. 5). Further, a drive pin associated with a drive bar of the drive assembly of the forceps may then be inserted through cam slots 412a, 412b and 422a, 422b to operably engage end effector assembly 400 with the drive assembly such that translation of the drive bar effects pivoting of the jaw members 410, 420 relative to one another, e.g., between spaced-apart and approximated positions.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 8:
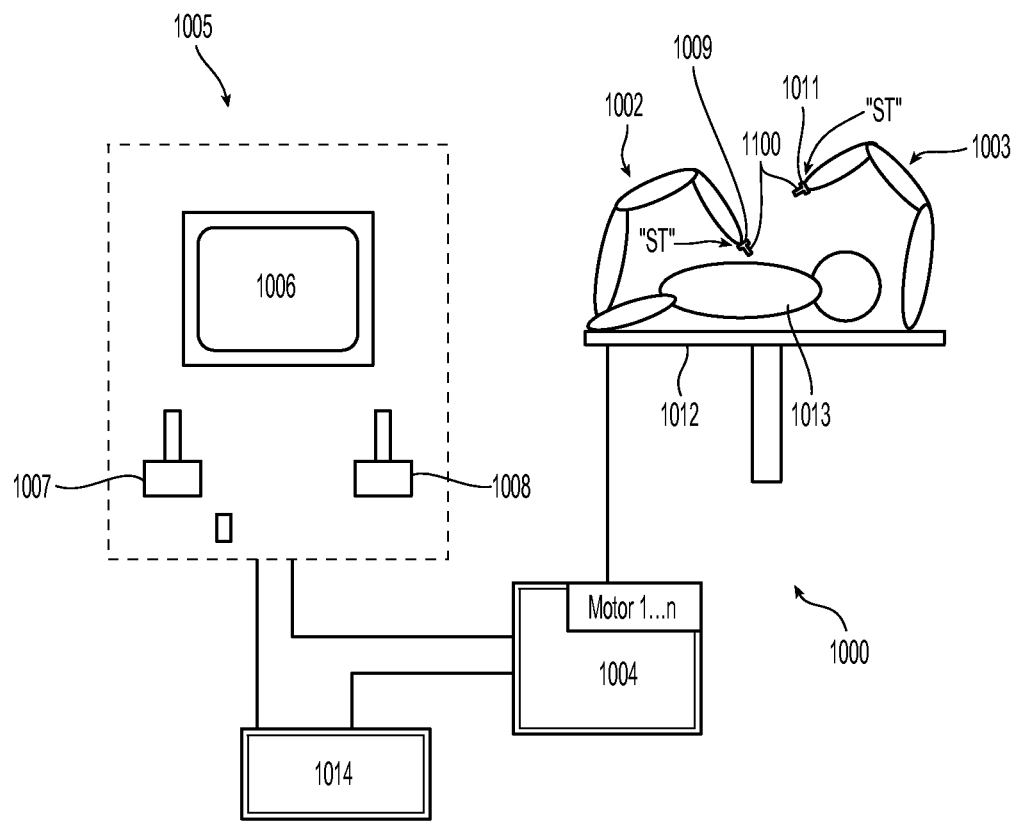
FIG. 8 is a schematic illustration of a robotic surgical system configured for use in conjunction with aspects and features of the present disclosure.

Referring to FIG. 8, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
a shell including a housing and a shaft extending distally from the housing, the shell including first and second shell components, each of the first and second shell components monolithically formed and including a housing portion and a shaft portion, the housing portions of the first and second shell components configured to engage one another to form the housing of the shell upon engagement of the first and second shell components with one another and the shaft portions of the first and second shell components configured to engage one another to form the shaft of the shell upon engagement of the first and second shell components with one another;
an end effector assembly operably coupled to the shaft at a distal end thereof;
a handle assembly operably coupled to the housing; and
a drive assembly disposed within the shell and operably coupled between the handle assembly and the end effector assembly such that actuation of the handle assembly manipulates the end effector assembly.

2. The surgical instrument according to claim 1, wherein each of the first and second shell components is a single molded piece.

3. The surgical instrument according to claim 1, wherein the housing portions of the first and second shell components each include a fixed handle portion extending therefrom, the fixed handle portions cooperating to define a fixed handle of the handle assembly upon engagement of the first and second shell components with one another.

4. The surgical instrument according to claim 3, wherein the handle assembly further includes a movable handle pivotably coupled between the housing portions and movable relative to the fixed handle.

5. The surgical instrument according to claim 1, wherein the first and second shell components each include engagement features to facilitate the engagement of the first and second shell components with one another.

6. The surgical instrument according to claim 1, wherein the first and second shell components each include support structures to facilitate the support of the drive assembly within the shell.

7. The surgical instrument according to claim 1, wherein the end effector assembly includes first and second jaw members, at least one of the first or second jaw members pivotable relative to the other between a spaced-apart position and an approximated position for grasping tissue therebetween.

8. The surgical instrument according to claim 7, wherein one of the first or second jaw members is fixed relative to the shaft and wherein the other of the first or second jaw members is movable relative to the fixed jaw member and the shaft between the spaced-apart and approximated positions.

9. The surgical instrument according to claim 8, wherein the fixed jaw member includes a proximal flange that is monolithically formed with the shaft portion of one of the first or second shell components.

10. The surgical instrument according to claim 8, wherein the fixed jaw member includes a proximal flange, the proximal flange including first and second flange components monolithically formed with the respective shaft portions of the first and second shell components, the first and second flange components configured to engage one another to form the proximal flange upon engagement of the first and second shell components with one another.

11. The surgical instrument according to claim 7, wherein at least one of the first or second jaw members is configured to engage the shaft via a peg-aperture engagement.

12. The surgical instrument according to claim 7, wherein at least one of the first or second jaw members is configured to engage the drive assembly via a pin-slot engagement or a peg-slot engagement.

13. The surgical instrument according to claim 7, wherein each of the first and second jaw members includes a "U"-shaped proximal flange portion, and wherein the "U"-shaped proximal flange portions of the first and second jaw members are configured to inter-fit with one another in an overlapping configuration.

14. The surgical instrument according to claim 1, wherein the shaft includes a pair of spaced-apart flanges extending from the distal end of the shaft and coupled to the shaft via living hinges, the spaced-apart flanges configured to flex relative to the shaft to facilitate engagement of the end effector assembly with the shaft.

* * * * *